(12) United States Patent
Yoshinaga

(10) Patent No.: US 11,357,880 B2
(45) Date of Patent: *Jun. 14, 2022

(54) WATER ABSORPTION TREATMENT MATERIAL AND METHOD FOR MANUFACTURING THE SAME

(71) Applicant: DAIKI CO., LTD., Tokyo (JP)

(72) Inventor: Junji Yoshinaga, Tokyo (JP)

(73) Assignee: DAIKI CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/951,746

(22) Filed: Nov. 18, 2020

(65) Prior Publication Data

US 2021/0069365 A1  Mar. 11, 2021

Related U.S. Application Data

(63) Continuation of application No. PCT/JP2019/018236, filed on May 7, 2019.

(30) Foreign Application Priority Data

Aug. 6, 2018 (JP) .............................. JP2018-147327

(51) Int. Cl.
 *A61L 9/014* (2006.01)
 *B01J 20/02* (2006.01)
 *A61L 101/26* (2006.01)

(52) U.S. Cl.
 CPC ........... *A61L 9/014* (2013.01); *B01J 20/0237* (2013.01); *A61L 2101/26* (2020.08); *A61L 2209/22* (2013.01)

(58) Field of Classification Search
 None
 See application file for complete search history.

(56) References Cited

FOREIGN PATENT DOCUMENTS

| EP | 1616911 A1 | 1/2006 |
|---|---|---|
| EP | 1806383 A1 | 7/2007 |
| EP | 1648966 B1 | 8/2015 |
| EP | 3165564 A1 | 5/2017 |
| EP | 3321313 A1 | 5/2018 |
| JP | H10-279822 A | 10/1998 |
| JP | 2004-261085 A | 9/2004 |
| JP | 2004261085 A * | 9/2004 |
| JP | 2005-279349 A | 10/2005 |
| JP | 2012-12455 A | 1/2012 |
| JP | 2016-42839 A | 4/2016 |
| JP | 2016-73247 A | 5/2016 |
| JP | 2018-14941 A | 2/2018 |
| WO | 2017/209339 A1 | 12/2017 |

OTHER PUBLICATIONS

Hiroshi, I. JP2004261085A—translated document (Year: 2004).*

(Continued)

*Primary Examiner* — Jelitza M Perez
(74) *Attorney, Agent, or Firm* — Oliff PLC

(57) ABSTRACT

A water absorption treatment material absorbs a liquid containing a malodorous substance, and includes a first grain and a second grain. The first grain contains a metal having a deodorizing function. The second grain does not contain a metal having a deodorizing function.

18 Claims, 4 Drawing Sheets

(56) References Cited

OTHER PUBLICATIONS

Aug. 13, 2019 Written Opinion issued in International Patent Application No. PCT/JP2019/018236.
Aug. 13, 2019 International Search Report issued in International Patent Application No. PCT/JP2019/018236.
Nov. 11, 2020 Third Party Observation issued in International Patent Application No. PCT/JP2019/018236.
Nov. 5, 2021 Office Action issued in Japanese Patent Application No. 2018-235349.

* cited by examiner

WATER ABSORPTION TREATMENT MATERIAL AND METHOD FOR MANUFACTURING THE SAME

CROSS REFERENCE TO RELATED APPLICATION

This is a Continuation of International Application No. PCT/JP2019/018236 filed May 7, 2019, which claims the benefit of Japanese Application No. 2018-147327 filed Aug. 6, 2018. The contents of these applications are hereby incorporated by reference in their entirety.

TECHNICAL FIELD

The present invention relates to a water absorption treatment material that absorbs a liquid containing a malodorous substance, and a method for manufacturing the same.

BACKGROUND ART

A conventional water absorption treatment material is disclosed in, for example, Patent Document 1. The water absorption treatment material disclosed in Patent Document 1 is an excrement treatment material that absorbs and treats excrement, and consists of a large number of grains having a water absorbing property. Each grain has a granular core portion, and a coating portion that covers the granular core portion. The granular core portion contains powder of an organic waste material, an adhesive material, and a metal compound. As the metal compound, a metal compound having a deodorizing function is used. The coating portion is formed of a mixture of paper powder and an adhesive material.

CITATION LIST

Patent Document
Patent Document 1: JP 2004-261085A

SUMMARY OF INVENTION

Technical Problem

In the water absorption treatment material described above, it is possible to suppress generation of an odor caused by excrement after use (after the excrement is absorbed), since the metal compound having the deodorizing function is contained. However, the fact that each grain contains the metal compound requires an increased amount of metal material used, which leads to an increase in the manufacturing cost of the water absorption treatment material.

Solution to Problem

The present invention has been made in view of the problems described above, and it is an object of the present invention to provide a water absorption treatment material that can be manufactured at a low cost and in which generation of an odor can be suppressed after use, and a method for manufacturing the same.

A water absorption treatment material according to the present invention is a water absorption treatment material that absorbs a liquid containing a malodorous substance. The water absorption treatment material includes: a first grain that contains a metal having a deodorizing function; and a second grain that does not contain the metal.

The water absorption treatment material includes the first and second grains. The first grain contains the metal having the deodorizing function. On the other hand, the second grain does not contain the metal. Because the metal is contained in only a part of the grains (first grain) as described above, it is possible to save the amount of metal material used. Moreover, the deodorizing action of the metal contained in the first grain is also exerted on the second grain around the first grain. For this reason, it is possible to suppress generation of odors caused not only by the liquid absorbed in the first grain but also by the liquid absorbed in the second grain.

A method for manufacturing a water absorption treatment material according to the present invention is a method for manufacturing a water absorption treatment material that absorbs a liquid containing a malodorous substance. The method includes: a first grain forming step of forming a first grain that contains a metal having a deodorizing function; and a second grain forming step of forming a second grain that does not contain the metal.

The manufacturing method includes the first and second grain forming steps. In the first grain forming step, the first grain that contains the metal having the deodorizing function is formed. On the other hand, in the second grain forming step, the second grain that does not contain the metal is formed. Because the metal is contained in only a part of the grains (first grain) as described above, it is possible to save the amount of metal material used. Moreover, in the manufactured water absorption treatment material, the deodorizing action of the metal contained in the first grain is also exerted on the second grain around the first grain. For this reason, it is possible to suppress generation of odors caused not only by the liquid absorbed in the first grain but also by the liquid absorbed in the second grain.

Advantageous Effects of Invention

According to the present invention, it is possible to implement a water absorption treatment material that can be manufactured at a low cost and in which generation of an odor can be suppressed after use, and a method for manufacturing the same.

DESCRIPTION OF EMBODIMENTS

Figure 1:
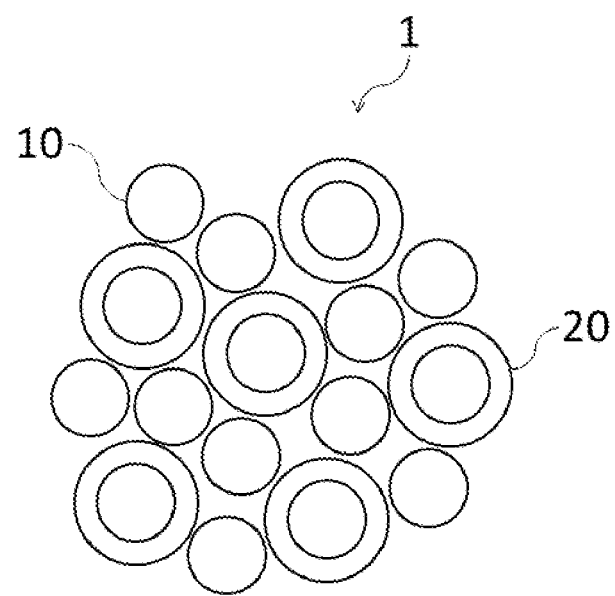
FIG. 1 is a schematic diagram of a water absorption treatment material according to an embodiment of the present invention.

Hereinafter, an embodiment of the present invention will be described in detail with reference to the drawings. In the description of the drawings, the same elements are given the same reference numerals, and a redundant description will be omitted.

FIG. 1 is a schematic diagram of a water absorption treatment material according to an embodiment of the present invention. A water absorption treatment material 1 is a water absorption treatment material that absorbs a liquid containing a malodorous substance, and includes a grain 10 (first grain) and a grain 20 (second grain). The grains 10 and 20 each have a water absorbing property, and absorb the liquid. The water absorption treatment material 1 is, for example, an excrement treatment material for absorbing excrement, a vomit treatment material for absorbing vomit, or a kitchen garbage treatment material for absorbing kitchen garbage (moisture contained in the kitchen garbage).

In the present embodiment, a plurality of the grains 10 and a plurality of the grains 20 are provided. In the water absorption treatment material 1, the grains 10 and the grains 20 are contained in a mixed manner. The number of the grains 10 is preferably 30% or more and 70% or less of the total number of the grains 10 and the grains 20, and more preferably 40% or more and 60% or less.

Figure 2:
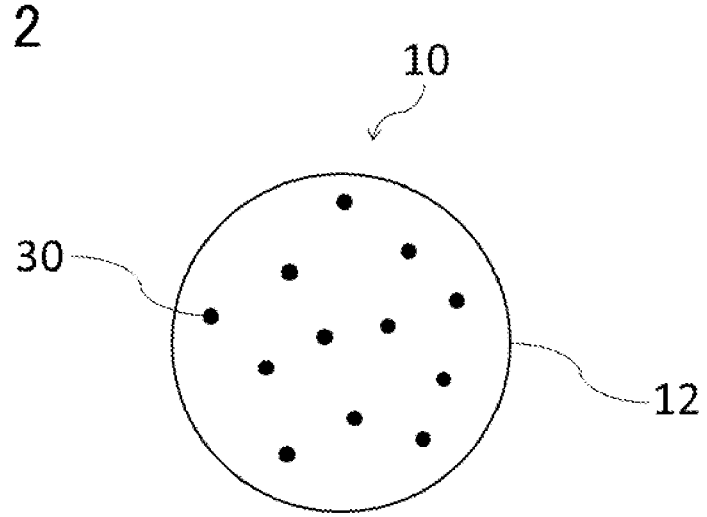
FIG. 2 is a schematic diagram of a grain 10.

FIG. 2 is a schematic diagram of the grain 10. The grain 10 contains a metal 30 and a water-absorbent material (first water-absorbent material). The grain 10 may be composed only of the metal 30 and the first water-absorbent material, or may be composed of these materials and another material. Note that "metal" includes metal ions in the present invention.

The metal 30 has a deodorizing function. As the metal 30, it is possible to use, for example, copper, silver, zinc, titanium, or the like. Preferably, the metal 30 is contained in the grain 10 in a state in which the metal 30 is carried on the first water-absorbent material. As used herein, the metal 30 carried on the first water-absorbent material refers to the metal 30 fixed on the first water-absorbent material by chemical bonding or physical bonding. The first water-absorbent material is the main material of the grain 10. As used herein, the main material of the grain 10 refers to one of the materials constituting the grain 10 that accounts for the highest weight ratio in the grain 10. The first water-absorbent material is preferably organic matter. Examples of the water-absorbent material of organic matter include cellulosic materials, plastics, and bean curd lees. The cellulosic materials include, for example, pulp, cotton, and rayon.

The grain 10 includes a core portion 12 (first core portion). The core portion 12 is in a granular shape. The granular shape may be, for example, spherical, cylindrical, elliptic, or the like. The core portion 12 has a function of absorbing and retaining a liquid. In the grain 10, the core portion 12 is uncovered. A coating portion is not formed on the core portion 12, and thus the entire surface of the core portion 12 is exposed. That is, the grain 10 is composed only of the core portion 12.

Figure 3:
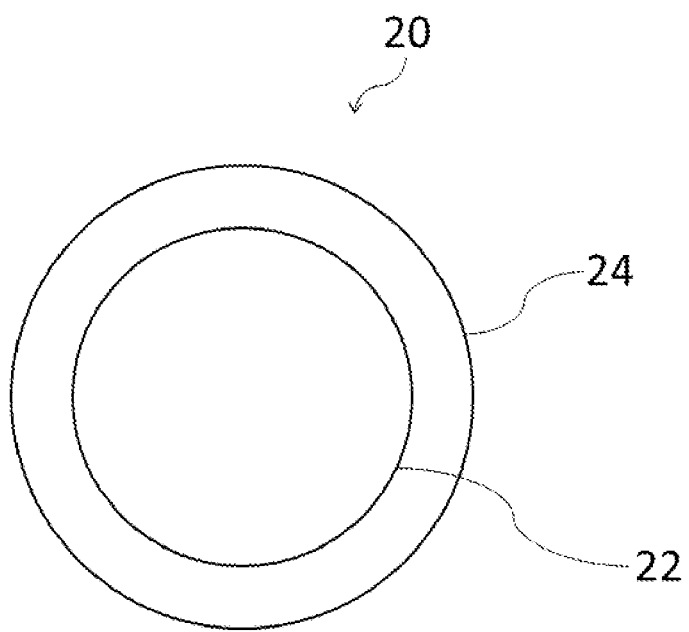
FIG. 3 is a schematic diagram of a grain 20.

FIG. 3 is a schematic diagram of the grain 20. The grain 20 does not contain a metal having a deodorizing function. Preferably, the grain 20 does not contain any metals including the metal having the deodorizing function. The grain 20 contains a water-absorbent material (second water-absorbent material). The second water-absorbent material may be a same material as the first water-absorbent material, or may be a different material from the first water-absorbent material.

The grain 20 includes a core portion 22 (second core portion) and a coating portion 24. The core portion 22 is in a granular shape. The core portion 22 has a function of absorbing and retaining a liquid. The core portion 22 contains the second water-absorbent material as its main material. The core portion 22 may be composed only of the second water-absorbent material, or may be composed of the second water-absorbent material and another material. The particle diameter of the core portion 22 may be the same as the particle diameter of the core portion 12, or may be different from the particle diameter of the core portion 12. As used herein, the particle diameter is defined as the diameter of the minimum sphere that can contain the core portion.

The coating portion 24 covers the core portion 22. The coating portion 24 may cover the entire surface of the core portion 22, or may cover only a part of the surface of the core portion 22. The coating portion 24 has a function of bonding the grains 10 and 20, and clumping them together when in use (when the water absorption treatment material 1 has absorbed a liquid to be treated). Also as the main material of the coating portion 24, the second water-absorbent material can be used. The coating portion 24 contains an adhesive material. As the adhesive material, it is possible to use, for example, starch, CMC (carboxymethyl cellulose), PVA (polyvinyl alcohol), dextrin, or a water-absorbent polymer. Note that the grain 10 does not contain an adhesive material in the present embodiment. As described above, in the water absorption treatment material 1, the grain 20 has a multi-layer structure composed of the core portion 22 and the coating portion 24, whereas the grain 10 has a single-layer structure composed only of the core portion 12.

Next, an example of a method for manufacturing the water absorption treatment material 1 will be described as an embodiment of the method for manufacturing a water absorption treatment material according to the present invention. The manufacturing method includes a first grain forming step, a second grain forming step, and a mixing step.

The first grain forming step is a step of forming the grain 10. This step includes a first core portion forming step. The first core portion forming step is a step of forming the core portion 12. In this step, a granule that will serve as the core portion 12 is formed by granulating a first core portion material (materials constituting the core portion 12) that contains the metal 30 and the first water absorbent material with a granulation apparatus. In the present embodiment, a plurality of the core portions 12 are formed. As the granulation apparatus, for example, an extrusion granulator can be used. Prior to granulation, the first core portion material is subjected to pre-treatment such as pulverization, kneading, and adding water, as needed. In the case where the metal 30 is to be carried on the first water-absorbent material, a fixing process is performed in which the metal 30 is fixed on the first water-absorbent material prior to granulation. Such a fixing process can be performed by known methods. The core portions 12 are not coated in the first grain forming step. Accordingly, the grains 10 in each of which the core portion 12 is uncovered are obtained.

The second grain forming step is a step of forming the grain 20. This step includes a second core portion forming step, and a coating portion forming step. The second core portion forming step is a step of forming the core portion 22. In this step, a granule that will serve as the core portion 22 is formed by granulating a second core portion material (material(s) constituting the core portion 22) that contains the second water-absorbent material with the granulation apparatus. In the present embodiment, a plurality of the core portions 22 are formed. Prior to granulation, the second core portion material is subjected to pre-treatment such as pulverization, kneading, and adding water, as needed.

The coating portion forming step is a step of forming the coating portion 24. In this step, the coating portion 24 is formed by attaching a powdery coating material (materials constituting the coating portion 24) to the surface of the core portion 22 with a coating apparatus or the like. The coating material contains the adhesive material. The coating material may be attached by, for example, sprinkling or spraying the coating material. In this way, the grains 20 in each of which the core portion 22 is covered by the coating portion 24 are obtained. Note that the first and second grain forming steps may be performed in arbitrary order. That is, the both steps may be performed simultaneously in parallel, or either step may be performed prior to the other step.

The mixing step is a step of mixing the grains 10 formed in the first grain forming step and the grains 20 formed in the second grain forming step. In this step, it is preferable to mix the grains 10 and the grains 20 such that the number of the grains 10 is 30% or more and 70% or less of the total number of the grains 10 and the grains 20. It is more preferable to mix the grains 10 and the grains 20 such that the number of the grains 10 is 40% or more and 60% or less of the total number of the grains 10 and the grains 20. In this step, the mixed grains 10 and 20 are preferably stirred. In this way, the water absorption treatment material 1 that includes the grains 10 and the grains 20 in a mixed manner is obtained.

Advantageous effects of the present embodiment will be described. In the present embodiment, the grain 10 that contains a metal having a deodorizing function (the metal 30), and the grain 20 that does not contain the metal are formed. Because the metal 30 is contained in only a part of the grains (the grain 10) as described above, it is possible to save the amount of metal material used. Moreover, it is considered that the deodorizing action of the metal 30 is due to the fact that the metal 30 is eluted into a liquid to be treated when in use, namely when the water absorption treatment material 1 has absorbed the liquid, and the eluted metal ions suppress activity of bacteria (trace metal action). Therefore, in the water absorption treatment material 1, the deodorizing action of the metal 30 contained in the grain 10 is also exerted on the grain 20 around the grain 10. For this reason, it is possible to suppress generation of odors caused not only by the liquid absorbed in the grain 10 but also by the liquid absorbed in the grain 20. Accordingly, the water absorption treatment material 1 that can be manufactured at a low cost and in which generation of an odor can be suppressed after use, and a method for manufacturing the same are implemented.

The grain 10 contains the water-absorbent material (first water-absorbent material) in addition to the metal 30. Accordingly, the grain 10 can be given the water absorbing property.

In the case where the metal 30 is contained in the grain 10 in the state in which the metal 30 is carried on the first water-absorbent material, a situation can be made unlikely to occur in which the metal 30 comes off from the grain 10 before use.

In the case where the first water-absorbent material is a cellulosic material, the water absorbing property of the grain 10 can be enhanced. Moreover, cellulosic materials have a large number of hydroxyl groups. For this reason, a large amount of the metal 30 can be carried on the first water-absorbent material (cellulosic material) by chemically bonding metal atoms between two hydroxyl groups.

In the case where the grain 10 is composed only of the metal 30 and the first water-absorbent material, the grain 10 having the water absorbing property while containing the metal 30 can be formed of minimum materials. This contributes to reduction in the procuring cost of the materials and eventually in the manufacturing cost of the water absorption treatment material 1.

The grain 20 contains the water-absorbent material (second water-absorbent material). Accordingly, the grain 20 can be given the water absorbing property.

In the case where the second water-absorbent material is s same material as the first water-absorbent material, one water-absorbent material can be used for both of the grain 10 and the grain 20. This also contributes to reduction in the procuring cost of the materials and eventually in the manufacturing cost of the water absorption treatment material 1.

In the case where copper is used as the metal 30, it is particularly advantageous in terms of persistence of the deodorizing action, safety and inexpensiveness.

The grain 10 does not contain an adhesive material. Accordingly, it is possible to save the amount of adhesive material used, which is relatively expensive, and further reduce the manufacturing cost of the water absorption treatment material 1. In contrast, in a case where an adhesive material exists in the grain 10, a liquid is less likely to reach the metal 30 when in use, and therefore the metal 30 is sometimes prevented from being eluted into the liquid. In the present embodiment, because the grain 10 does not contain an adhesive material, it is possible to make it easy to elute the metal 30 into the liquid when in use. However, it is not required that the grain 10 does not contain an adhesive material.

In the grain 10, the core portion 12 is uncovered. That is, the core portion 12 is not coated. Accordingly, it becomes easy for metal ions that have been eluted from the metal 30 contained in the core portion 12 to reach the surrounding grain 20 when in use.

On the other hand, in the grain 20, the core portion 22 is covered by the coating portion 24 containing the adhesive material. By providing only a part of the grains (the grain 20) with the coating portion as described above, it is possible to save the coating material. Also, the bonding action of the coating portion 24 provided in the grain 20 is also exerted on the grain 10 around the grain 20. For this reason, even though the grain 10 is not provided with a coating portion, a clump composed of used grains 10 and 20 is formed. Accordingly, it is possible to obtain a clump of the grains 10 and 20 after use while saving the coating material.

In the case where the particle diameter of the core portion 22 is the same as the particle diameter of the core portion 12, it becomes possible to use the same granulation apparatus for forming the core portion 12 and the core portion 22. On the other hand, in the case where the particle diameter of the core portion 22 is different from the particle diameter of the core portion 12, it is possible to increase freedom in design for the particle diameter of the core portion 12. That is, the particle diameter of the core portion 12 can be greater than the particle diameter of the core portion 22, and can be less than the particle diameter of the core portion 22.

From the viewpoint of saving the metal material and achieving reduction in the manufacturing cost, it is advantageous that the grains 10 account for a smaller proportion in the entire water absorption treatment material 1. From this viewpoint, the number of the grains 10 is preferably 70% or less of the total number of the grains 10 and the grains 20, and more preferably 60% or less. If, on the other hand, the proportion of the grains 10 is too small, the deodorizing action of the metal 30 will be insufficient, which may cause insufficiency of the deodorizing effect of the water absorption treatment material 1. From this viewpoint, the number of the grains 10 is preferably 30% or more of the total number of the grains 10 and the grains 20, and more preferably 40% or more.

The present invention is not limited to the embodiment described above, and various modifications can be made. In the embodiment described above, the grain 10 may be configured to collapse when absorbing a liquid. Such grain 10 can be realized by reducing the compressive force that is applied to the first core portion material during granulation. For example, the compressive force applied to the first core portion material can be reduced by reducing the thickness of a die of an extrusion granulator. In the case where the grain 10 collapses when in use in such way, it is possible to expose the metal 30 that has been hidden inside the grain 10 to the outside. Thus, it is possible to bring out the deodorizing action of the metal 30 more efficiently.

Figure 4:
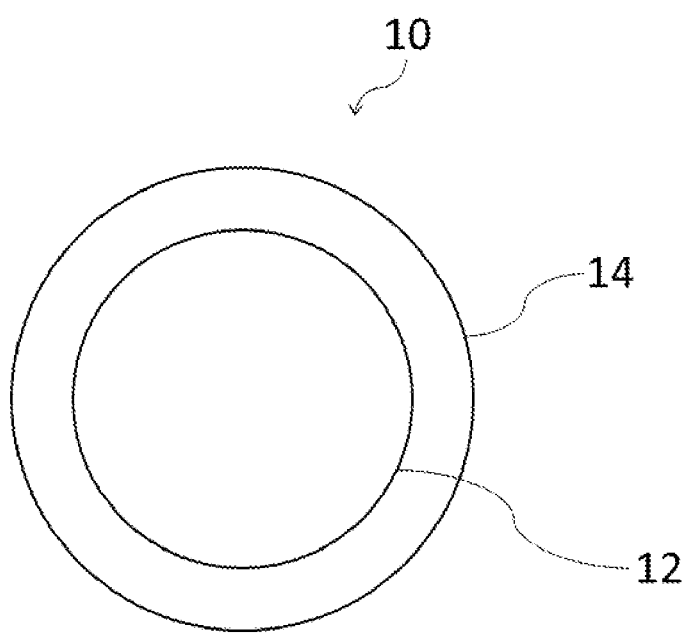
FIG. 4 is a schematic diagram of the grain 10 according to a modified example.

In the embodiment described above, an example is given in which the core portion 12 is uncovered in the grain 10. However, the core portion 12 may be covered by the coating portion 14 as shown in FIG. 4. That is, the grain 10 may have a multi-layer structure composed of the core portion 12 and the coating portion 14. In that case, the metal 30 may be contained in both of the core portion 12 and the coating portion 14, or may be contained in either one of the core portion 12 and the coating portion 14. The metal 30 is not shown in FIG. 4. The configuration of the coating portion 14 is the same as the configuration of the coating portion 24, except that the coating portion 14 may contain the metal 30.

In the embodiment described above, an example is given in which the grain 20 is provided with the coating portion 24. However, it is not required that the grain 20 is provided with the coating portion 24. That is, the grain 20 may have a single-layer structure composed only of the core portion 22.

LIST OF REFERENCE NUMERALS

1 Water Absorption Treatment Material
10 Grain (First Grain)
12 Core Portion (First Core Portion)
14 Coating Portion
20 Grain (Second Grain)
22 Core Portion (Second Core Portion)
24 Coating Portion
30 Metal

The invention claimed is:

1. A water absorption treatment material that absorbs a liquid containing a malodorous substance, the water absorption treatment material comprising:
   a first grain that contains a metal having a deodorizing function, the first grain including an uncovered first core portion having a granular shape, and
   a second grain that does not contain the metal, the second grain including a second core portion having a granular shape, and the second grain including a coating portion that covers the second core portion, the coating portion having an adhesive material.

2. The water absorption treatment material according to claim 1, wherein the first grain further contains a first water-absorbent material.

3. The water absorption treatment material according to claim 2, wherein the metal is contained in the first grain in a state in which the metal is fixed to the first water-absorbent material.

4. The water absorption treatment material according to claim 2, wherein the first water-absorbent material is a cellulosic material.

5. The water absorption treatment material according to claim 4, wherein the cellulosic material is pulp, cotton or rayon.

6. The water absorption treatment material according to claim 2, wherein the first grain is composed only of the metal and the first water-absorbent material.

7. The water absorption treatment material according to claim 2, wherein the second grain contains a second water-absorbent material.

8. The water absorption treatment material according to claim 7, wherein the second water-absorbent material is a same material as the first water-absorbent material.

9. The water absorption treatment material according to claim 1, wherein the metal contained in the first grain is copper.

10. The water absorption treatment material according to claim 1, wherein the first grain does not contain an adhesive material.

11. The water absorption treatment material according to claim 1, wherein the first grain collapses when absorbing the liquid.

12. The water absorption treatment material according to claim 1, wherein a particle diameter of the second core portion is the same diameter as a particle diameter of the first core portion.

13. The water absorption treatment material according to claim 1, wherein a particle diameter of the second core portion is different from a particle diameter of the first core portion.

14. The water absorption treatment material according to claim 1, wherein the adhesive material is a water-absorbent polymer.

15. A method for manufacturing a water absorption treatment material that absorbs a liquid containing a malodorous substance, the method comprising:
   a first grain forming step of forming a first grain that contains a metal having a deodorizing function, the first grain including an uncovered first core portion having a granular shape, and
   a second grain forming step of forming a second grain that does not contain the metal, the second grain including a second core portion having a granular shape, and the second grain including a coating portion that covers the second core portion, the coating portion having an adhesive material.

16. The method for manufacturing the water absorption treatment material according to claim 15, wherein in the first grain forming step, the first grain is further formed to contain a first water-absorbent material.

17. The method for manufacturing the water absorption treatment material according to claim 16, wherein in the first grain forming step, the first grain is formed to be composed of only of the metal and the first water-absorbent material.

18. The method for manufacturing the water absorption treatment material according to claim 15, wherein the metal contained in the first grain is copper.

* * * * *